United States Patent [19]

Michel et al.

[11] Patent Number: 5,741,654
[45] Date of Patent: Apr. 21, 1998

[54] IMMUNOASSAY FOR THE DETECTION OF HUMAN AUTOANTIBODIES

[75] Inventors: Gerd Michel, Heidelberg; Hans-Bertram Braun, Weisbaden; Kay Röhrig, Wiesbadem; Birgit Thome-Kromer, Oberursel, all of Germany

[73] Assignee: Abbott Laboratories, Abbott Park, Ill.

[21] Appl. No.: 637,801

[22] PCT Filed: Oct. 28, 1994

[86] PCT No.: PCT/EP94/03550

§ 371 Date: May 2, 1996

§ 102(e) Date: May 2, 1996

[87] PCT Pub. No.: WO95/12816

PCT Pub. Date: May 11, 1995

[30] Foreign Application Priority Data

Nov. 2, 1993 [EP] European Pat. Off. ............ 93117725

[51] Int. Cl.$^6$ ..................... G01N 33/53; G01N 33/544; G01N 33/536; C12Q 1/42
[52] U.S. Cl. ................... 435/7.9; 435/4; 435/7.1; 435/21; 436/528; 436/435; 436/536
[58] Field of Search .................... 435/4, 7.1, 7.9, 435/21; 436/528, 535, 536

[56] References Cited

U.S. PATENT DOCUMENTS 4,689,310 8/1987 Kramer et al. .
5,200,315 4/1993 Sutton et al. .

FOREIGN PATENT DOCUMENTS 0424633 2/1991 European Pat. Off. .
0424634 2/1991 European Pat. Off. .

OTHER PUBLICATIONS

M. Manns et al., *Journal of Clinical Laboratory Analysis*, vol. 1(4), 344–352 (1987), No Title.
M. Manns, *Seminars in Liver Disease*, vol. 11(3), 205–214 (1991) No Title.
M. Manns et al., *Clinical and Experimental Immunology*, lvol. 57 (3), 600–608 (1984) No Title.
M Ruiz–Moreno et al., *Jounal of Hepatology*, vol. 12(2), 265–266 (1991) No Title.
M. Gueguen et al., *Biochemical and Biophysical Research Communications*, vol. 159(2), 542–547 (1989) No Title.
R. Seelig et al., *Clinical and Experimental Immunology*, vol. 92(3), 373–380, (1993) No Title.
Seelig et al. Anti–LKM–1 Antibodies Determined by use of Recombinant P450 2D6 in Elisa and Western Blot and Their Association with Anti–HCVand HCV–RNA, CLIN. Immuno L. 92(3): 373–380, 1993.
Sigma Chemical Company Catalog, p. 1183—1992.

*Primary Examiner*—James C. Housel
*Assistant Examiner*—Rodney P. Swartz
*Attorney, Agent, or Firm*—Andreas M. Danckers

[57] ABSTRACT

An assay and test kit of the determination of LKM-1 autoantibodies in test samples suspected of containing anti-LKM-1 autoantibodies. The method uses a solid phase which preferably is a microparticle. The method is standardized and can be performed in automated systems, allowing quantitation of the amount of anti-LKM antibody in test samples.

9 Claims, 6 Drawing Sheets

IMMUNOASSAY FOR THE DETECTION OF HUMAN AUTOANTIBODIES

BACKGROUND OF THE INVENTION

This invention relates generally to autoantibodies, and more particularly, relates to an immunoassay for the detection of liver-kidney microsomal (LKM) autoantibodies by automated or semi-automated means.

Liver-kidney microsomal (LKM) autoantibodies are known to be associated with inflammatory liver diseases. LKM autoantibodies associated with idiopathic autoimmune chronic active hepatitis (AI-CAH) are termed "LKM-1" autoantibodies. M. P. Manns, in *Seminars in Liver Disease*, Vol. II, No. 3:205–214 (1991).

The LKM-1 autoantibody has been found to recognize a 50 kilodalton (kDa) protein identified initially as rat liver cytochromes P450 db1 and db2, leading to the development of a method for determining LKM-1 in individuals. M. Gueguen et al., *Biochemical and Biophysical Research Communications* Vol. 159 (2):542–547 (1989). Recent reports indicate that three P450 cytochromes can be identified as autoantigens in patients with inflammatory liver disease. All three P450 cytochromes (IA2, IID6 and IIC9) are drug metabolizing enzymes recognized by strongly inhibitory autoantibodies. M. P. Manns et al., *Archives of Biochemistry and Biophysics* Vol. 280 (1):229–232 (1990).

Circulating autoantibodies such as LKM-1 have become important markers for determining the diagnosis of autoimmune hepatitis. The diagnosis of autoimmune hepatitis has become important, since patients suffering from autoimmune hepatitis benefit from treatment with immunosuppressives but not from treatment with interferons, used in the treatment of viral-induced hepatitis. Thus, the differentiation between viral-induced hepatitis and autoimmune hepatitis is important to ensure correct treatment. Recent reports have indicated that patients diagnosed with chronic non-A, non-B viral hepatitis (NANBH) by either exclusionary methods or assays for hepatitis C virus (HCV) and treated with interferon, actually were suffering from autoimmune hepatitis. M. Ruiz-Moreno et al., *J. Hep. Hepatol.*, Vol. 12 (2).:265–266 (1991), and T. Papo et al., *Annals of Internal Medicine* Vol. 116 (1):51–53 (1992). These recent reports have suggested that a diagnosis of autoimmune hepatitis should at least be considered before beginning interferon therapy, since this therapy is contraindicated for patients suffering from autoimmune hepatitis.

Historically, methods for detection of LKM-1 autoantibodies included indirect fluorescent antibody (IFA) techniques, radioimmunoassay (RIA), electromicroscopy and immunoblotting. M. Manns et al., *J. Clin. Lab. Analysis* 1:344–352 (1987), Manns et al., *Clin. Exp. Immunol.* Vol. 57: 600–608 (1984). Recently, enzyme-linked immunosorbent assays (ELSIA) have been reported. M. Gueguen et al., *Biochemical and Biophysical Research Communications* Vol. 159 (2):542–547 (1989). Traditionally, such ELISAs either have included the purification of the IgG fraction of an LKM-positive reference serum (negative for other autoantibodies), the coating of the IgG fraction to solid surfaces, and the reaction of the so-prepared solid phase with the test sample, or these ELISA assays have attempted to detect antibody to a particular cytochrome. However, while patients diagnosed with autoimmune hepatitis react with the 50 kDa antigen they may not react with a particular cytochrome.

While these known methods have provided researchers with various techniques to determine the presence of LKM autoantibodies, these techniques have been hampered by manual methods and non-standardization and subjective evaluations which make these techniques semiquantitative at best. It would be advantageous to provide an improved immunoassay for autoantibodies to LKM, which method would be quantitative, standardized, highly reproducible and time-saving. Such a standardized immunoassay would be useful not only for differential diagnosis but also for monitoring immunosuppressive therapy of patients diagnosed with autoimmune hepatitis disease.

SUMMARY OF THE INVENTION

The present invention provides an automated method for determining the presence of LKM autoantibodies in a test sample, which method comprises (a) incubating the test sample with an LKM specific binding member attached to a solid phase for a time and under conditions sufficient for LKM antigen/anti-LKM antibody specific binding pairs to form; (b) incubating with the so-formed specific binding pairs an indicator reagent comprising a species-specific antibody attached to a signal generating compound capable of generating a measurable signal; (c) measuring the signal detected, wherein the amount of signal detected is correlated to the amount of anti-LKM antibody present in the test sample. The solid phase can be a suspension of microparticles having affixed thereto an LKM-1 antigen selected from the group consisting of an LKM microsome fraction or LKM-1 (cytochrome P450 db 1) amino acids 125–497. Also, the test sample may be diluted prior to performing step (a). The mixture formed after step (a) can be separated by microparticle separation on a porous element followed by washing of the solid phase. In a preferred embodiment, the signal generating compound of the indicator reagent of step (b) is alkaline phosphatase and the species-specific antibody is goat anti-human IgG.

The present invention also provides a test kit for performing a LKM-1 autoantibody assay. The test kit comprises a container containing LKM antigen bound to a solid phase; and a container containing an indicator reagent capable of generating a measurable signal. In a preferred embodiment, the solid phases are microparticles to which an LKM antigen selected from the group consisting of an LKM microsome fraction or LKM-1 (cytochrome P450 db 1) amino acids 125–497 are attached. Also preferred is an indicator reagent comprising goat anti-human IgG attached to alkaline phosphatase.

DETAILED DESCRIPTION OF THE INVENTION

Figure 1:
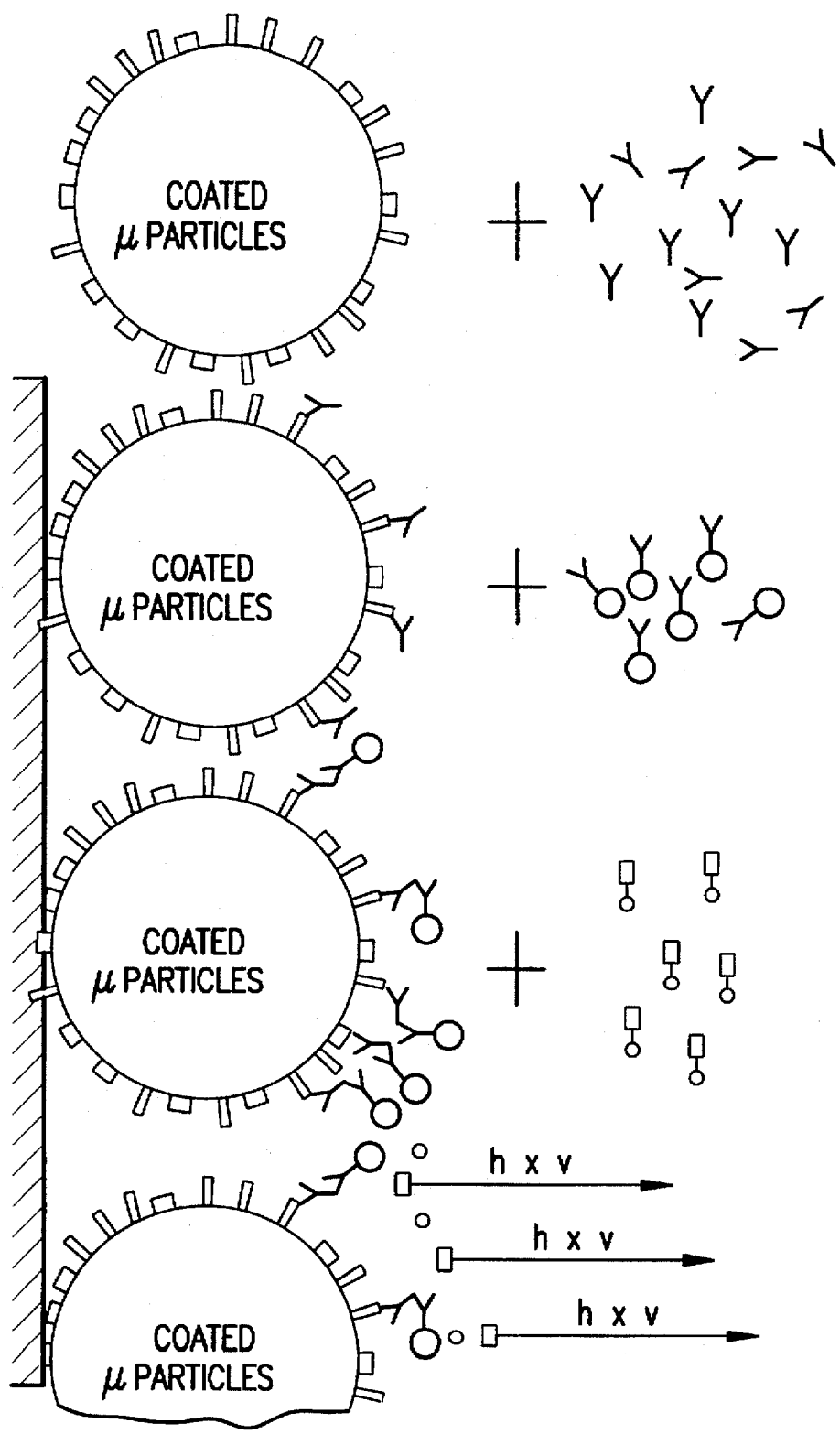
FIG. 1 is a schematic description of the LKM assay principle.

The present invention provides an improved immunoassay for the detection and quantitation of an analyte, LKM autoantibodies, in rest sample. Generally, a specific binding partner for LKM autoantibody is attached to a solid surface prior to assay. The so-prepared solid phase then is contacted with a test sample suspected of containing LKM autoantibodies to form a first mixture, and incubated for a time and under conditions sufficient to form LKM antigen/LKM autoantibody complexes. Next, an indicator reagent comprising a specific binding member for the antibody or a specific binding member to the complex and a signal generating compound are contacted with the antigen/antibody complex to form a second mixture. This second mixture is contacted for a time and under conditions sufficient to form antigen/antibody/indicator reagent complexes. The quantity of LKM antibodies present in the test sample is proportional to the amount of signal detected.

A "specific binding member," as used herein, is a member of a specific binding pair. That is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding member, for example, an analyte-analog. Immunoreactive specific binding members include antigens, antigen fragments antibodies and antibody fragments, both monoclonal and polyclonal; and complexes thereof, including those formed by recombinant DNA methods.

"Analyte," as used herein, is the substance to be detected which may be present in the test sample. The analyte can be any substance for which there exists a naturally occurring specific binding member (such as, an antigen), or for which a specific binding member can be prepared. Thus, an analyte is a substance that can bind to one or more specific binding members in an assay. "Analyte" also includes any antigen substances, haptens, antibodies, and combinations thereof. As a member of a specific binding pair, the analyte can be detected by means of naturally occurring specific binding partners (pairs) such as the use of intrinsic factor protein in the capture and/or indicator reagents for the determination of vitamin B12, or the use of a lectin in the capture and/or indicator reagents for the determination of a carbohydrate. The analyte can include a protein, a peptide, an amino acid, a hormone, asteroid, a vitamin, a drug including those administered for therapeutic purposes as well as those administered for illicit purposes, a bacterium, a virus, and metabolites of or antibodies to any of the above substances.

"Test samples" which can be tested by the methods of the present invention described herein include biological fluids such as whole blood, serum, plasma, cerebral spinal fluid, urine, ascites or any other body constituents or any tissue culture supernatants which might contain the antibodies of interest.

A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is mobilized upon (attached to) the solid phase and which has the ability to mobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, and other configurations known to those of ordinary skill in the art.

It is contemplated and within the scope of the invention that the solid phase also can comprise any suitable porous material with sufficient porosity to allow access by detection antibodies and a suitable surface affinity to bind antigens. Microporous structures are generally preferred, but materials with gel structure in the hydrated state may be used as well. Such useful solid supports include: natural polymeric carbohydrates and their synthetically modified, crosslinked or substituted derivatives, such as agar, agarose, cross-linked alginic acid, substituted and cross-linked gnar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, or plates, or they may be coated onto or bonded or laminated to appropriate inert carriers, such as paper, glass, plastic films, or fabrics.

The porous structure of nitrocellulose has excellent absorption and adsorption qualities for a wide variety of reagents including monoclonal antibodies. Nylon also possesses similar characteristics and also is suitable.

It is contemplated that such porous solid supports described hereinabove are preferably in the form of sheets of thickness from about 0.01 to 0.5 mm, preferably about 0.1 mm. The pore size may vary within wide limits, and is preferably from about 0.025 to 15 microns, especially from about 0.15 to 15 microns. The surfaces of such supports may be activated by chemical processes which cause covalent linkage of the antigen or antibody to the support. The irreversible binding of the antigen or antibody is obtained, however, in general, by adsorption on the porous material by poorly understood hydrophobic forces.

Preferred solid phase materials for flow-through assay devices include filter paper such as a porous fiberglass material or other fiber matrix materials. The thickness of such material is not critical and will be a matter of choice, largely based upon the properties of the sample or analyte being assayed, such as the fluidity of the test sample.

To change or enhance the intrinsic charge of the solid phase, a charged substance can be coated directly to the material or onto microparticles which then are retained by a solid phase support material. Alternatively, microparticles can serve as the solid phase, by being retained in a column or being suspended in the mixture of soluble reagents and test sample, or the particles themselves can be retained and mobilized by a solid phase support material. By "retained and mobilized" is meant that the particles on or in the support material are not capable of substantial movement to positions elsewhere within the support material. The particles can be selected by one skilled in the art from any suitable type of particulate material and include those composed of polystyrene, polymethylacrylate, polypropylene, latex, polytetrafluoroethylene, polyacrylonitrile, polycarbonate, or similar materials. The size of the particles is not critical, although it is preferred that the average diameter of the particles be smaller than the average pore size of the support material being used. Thus, embodiments which utilize various other solid phases also are contemplated and are within the scope of this invention. For example, ion capture procedures for immobilizing an immobilizable reaction complex with a negatively charged polymer, described in co-pending U.S. patent application Ser. No. 150,278 corresponding to EP Publication No. 0326100, and U.S. patent application Ser. No. 375,029 (EP Publication No. 0406473), can be employed according to the present invention to effect a fast solution-phase immunochemical reaction. An immobilizable immune complex is separated from the rest of the reaction mixture by ionic interactions between the negatively charged polyanion/immune complex and the previously treated, positively charged porous matrix and detected by using various signal generating systems previously described, including those described in chemiluminescent signal measurements as described in co-pending U.S. patent application Ser. No. 921,979 corresponding to EPO Publication No. 0 273,115.

Also, the methods of the present invention can be adapted for use in systems which utilize microparticle technology including automated and semi-automated systems wherein the solid phase comprises a microparticle. Such systems include those described in pending U.S. patent application Ser. No. 425,651 and U.S. Pat. No. 5,089,424, which correspond to published EPO applications Nos. EP 0 425 633 and EP 0 424 634, respectively, and U.S. Pat. No. 5,006,309.

The "indicator reagent" may comprise a signal generating compound (label) which is capable of generating a measurable signal detectable by external means conjugated (attached) to a specific binding member for LKM autoantibody. "Specific binding member," as used herein, means a member of a specific binding pair. That is, two different molecules where one of the molecules through chemical or physical means specifically binds to the second molecule. In addition to being an antibody or antibody fragment member of a specific binding pair for LKM autoantibody, the indicator reagent also can be a member of any specific binding pair, including either hapten-anti-hapten systems such as biotin or antibiotin, avidin or biotin, a carbohydrate or a lectin, a complementary nucleotide sequence, an effector or a receptor molecule, an enzyme cofactor and an enzyme, an enzyme inhibitor or an enzyme, and the like.

The various signal generating compounds (labels) contemplated include chromogens; catalysts such as enzymes, for example, alkaline phosphatase, horseradish peroxidase, beta-galactosidase and the like; luminescent compounds such as fluorescein and rhodamine; chemiluminescent compounds such as acridinium, phenanthridinium, dioxetanes, luminol and the like; radioactive elements; and direct visual labels including colored solid phases and colored microparticles. The selection of a particular label is not critical, but it will be capable of producing a signal either by itself or in conjunction with one or more additional substances.

In a first embodiment, the present invention provides an immunoassay for determining the presence and amount of LKM autoantibodies, which immunoassay comprises the steps of (a) contacting a test sample with LKM antigen, preferably the microsome fraction (described herein below), and incubating the so-formed mixture for a time and under conditions sufficient to form LKM antigen/antibody complexes; (b) contacting the LKM antigen/antibody complexes with an indicator reagent which comprises an anti-human antibody or a fragment thereof attached to a signal generating compound, which signal generating compound is capable of generating a detectable measurable signal, and incubating this second so-formed mixture for a time and under conditions sufficient to form LKM antigen/antibody/indicator reagent complexes; and (c) detecting the measurable signal generated by the signal generating compound as an indication of the presence of LKM autoantibody in the test sample. Preferably, the capture antigen for LKM autoantibody is attached to a solid phase prior to its use in the assay. If a solid phase is used, it can be separated from the liquid phase prior to the detection of the signal generating compound. Moreover, steps (a) and (b) can be performed simultaneously. It also is contemplated and within the scope of the invention that the test sample can be diluted in all of the assay embodiments, and that washing occurs or can occur between steps of all assay formats described herein.

Alternatively, the test sample for LKM autoantibody is contacted with LKM antigen, preferably the microsome fraction, and incubated for a time and under conditions sufficient for LKM antigen/antibody complexes to form. Next, the LKM antigen/antibody complexes are contacted with a solid phase capture reagent which comprises an previously reactive LKM antibody which specifically binds LKM antigen. The complexes and solid phase are incubated for a time and under conditions sufficient to form LKM antibody/antigen/antibody complexes. Then, the solid phase capture reagent is separated from the so-formed reaction mixture and contacted with an indicator reagent comprising a monoclonal or a polyclonal anti-LKM antibody or a fragment thereof which has been attached to a signal generating compound capable of generating a measurable signal, to form a mixture. This mixture is incubated for a time and under conditions sufficient to form LKM antibody/antigen/antibody/indicator reagent complexes. The presence of immobilized antibody is determined by detecting the measurable signal generated. A decrease in the amount of signal generated, as compared to an initial screening, confirms the presence of LKM autoantibody present in the test sample.

In another embodiment, a suitable LKM antigen, preferably the microsome fraction, is immobilized on a nitrocellulose membrane. The antigen also can be conjugated or crosslinked to itself, peptides or to various carrier proteins such as BSA, keyhole limpet hemocyanin, ovalbumin, and the like, before immobilization on the nitrocellulose membrane. Next, the test sample is incubated on the membrane for a time and under conditions sufficient for LKM antigen/antibody complexes to form. After removing unbound proteins, the membrane is incubated with an indicator reagent comprising anti-human antibodies labelled with a signal generating compound. The presence and/or amount of LKM autoantibody present in the test sample is determined by detecting the measurable signal. The amount of signal is proportional to the amount of anti-LKM present in a test sample.

Other embodiments which utilize various other solid phases also are contemplated and are within the scope of this invention. For example, ion capture procedures for immobilizing an immobilizable reaction complex with a negatively charged polymer, described in co-pending U.S. patent application Ser. No. 150,278 corresponding to EP publication 0 326 100, and U.S. patent application Ser. No. 375,029 (EP publication No. 0 406 473) both of which enjoy common ownership and are incorporated herein by reference, can be employed according to the present invention to effect a fast solution-phase immunochemical reaction. An immobilizable immune complex is separated from the rest of the reaction mixture by ionic interactions between the negatively charged poly-anion/immune complex and the previously treated, positively charged porous matrix and detected by using various signal generating systems previously described, including those described in chemiluminescent signal measurements as described in co-pending U.S. patent application Ser. No.921,979 corresponding to EPO Publication No. 0 273 115, which enjoys common ownership and which is incorporated herein by reference.

Also, the methods of the present invention can be adapted for use in systems which utilize microparticle technology including automated and semi-automated systems wherein the solid phase comprises a microparticle. Such systems include those described in pending U.S. patent application Ser. Nos. 426,651 and 426,643, which correspond to published EPO applications Nos. EP 0 425 633 and EP 0 424 634, respectively, which are incorporated herein by reference.

Preferably, a microparticle-based sandwich immunoassay for LKM-1 autoantibody is performed according to this invention, as follows: A test sample which may contain anti-LKM-1 autoantibody is contacted with microparticles coated with either an LKM microsome fraction or a recombinant protein comprising LKM-1 (cytochrome P450 db 1), amino acids 125–497. This mixture is incubated for a time and under conditions sufficient to form LKM antigen/anti-LKM antibody complexes. The so-formed reaction mixture then may either be transferred to a glass matrix (described herein) wherein the solid phase is retained and immobilized on the glass fiber matrix and excess reaction fluid is washed through, or reacted in the same vessel. Next, an indicator reagent (or so-called conjugate) comprising anti-human IgG and a measurable signal generating compound is added to the glass fiber matrix, and this second reaction mixture is incubated for a time and under conditions sufficient for LKM antigen/anti-LKM antibody/indicator reagent complexes to form. If the microparticles were not yet separated onto the glass fiber matrix, this separation step now occurs, and the mixture is washed. An alkaline phosphatase substrate, MUP, then is added to the separated particles and is allowed to react. The amount of measurable signal generated is an indication of the amount of anti-LKM autoantibodies present in the test sample by comparing the rate of formation of fluorescent product to the cutoff rate, which is determined by the index calibrator rate.

Also, the concentration or level of LKM autoantibodies present in a test sample can be accurately quantified in a fluorescence polarization immunoassay (FPIA) by employing the reagents and immunoassay method of the present invention. Examples of commercially available automated instruments with which fluorescence polarization assays can be conducted include: IMx® system, TDx® system, and TDxFLx™ system (all available from Abbott Laboratories, Abbott Park, Ill.). To perform a FPIA for the specific quantification of LKM autoantibodies, calibration curves using known mount of LKM autoantibodies were generated for measuring the amount of LKM autoantibodies in the test sample. When performing a fluorescence polarization immunoassay for the specific quantification of LKM autoantibody as described herein, the detectable moiety component of the tracer is a fluorescent moiety such as fluorescein, aminofluorescein, carboxyfluorescein, and the like, preferably 5 and 6-aminomethylfluorescein, 5 and 6-aminofluorescein, 6-carboxyfluorescein, 5-carboxyfluorescein, thioureafluorescein, and methoxytriazinolyl-aminofluorescein, and similar fluorescent derivatives. The fluorescent tracer can be used in combination with an antibody which is capable of binding both the tracer and LKM autoantibodies. For a competitive immunoassay the tracer and LKM autoantibody must be able to competitively bind to an LKM antigen. For the quantification of LKM autoantibody, the antigen reagent comprises microsome fragments containing LKM which are capable of binding to or recognizing LKM autoantibodies.

The amount of tracer bound to the antibody varies inversely to the amount of LKM autoantibody present in the test sample. Accordingly, the relative binding affinities of LKM autoantibody and the tracer to the antibody binding site are important parameters of the assay system.

Generally, fluorescent polarization techniques are based on the principle that a fluorescent tracer, when excited by plane polarized light of a characteristic wavelength, will emit light at another characteristic wavelength (i.e., fluorescence) that retains a degree of the polarization relative to the incident stimulating light that is inversely related to the rate of rotation of the tracer in a given medium. As a consequence of this property, a tracer substance with constrained rotation, such as in a viscous solution phase or when bound to another solution component such as an antibody with a relatively lower rate of rotation, will retain a relatively greater degree of polarization of emitted light than if in free solution.

When performing a fluorescent polarization immunoassay for the specific quantification of LKM autoantibody according to the present invention, a test sample suspected of containing thyroxine is contacted with antiserum or monoclonal antibodies prepared with immunogens according to the present invention, in the presence of labelled reagent of the present invention, which is capable of producing a detectable fluorescence polarization response to the presence of antiserum or monoclonal antibodies prepared with immunogens according to the present invention. Plane polarized light is then passed through the solution to obtain a fluorescent polarization response and the response is detected as a measure of mount of thyroxine present in the test sample.

The LKM microsome fragments of the present invention can be employed to prepare immunogens by coupling them to conventional carrier materials, and subsequently used to obtain antibodies.

The use of scanning probe microscopy (SPM) for immunoassays also is a technology to which the assay method of the present invention is easily adaptable. In scanning probe microscopy, in particular in atomic force microscopy, the capture phase, for example, the LKM microsome fragment, is adhered to a solid phase, the test sample then is placed in contact with the solid phase, and a scanning probe microscope is utilized to detect antigen/antibody complexes which may be present on the surface of the solid phase. Quantification is possible in system such as SPM. The use of scanning probe microscopy eliminates the need for labels which normally must be utilized in many immunoassay systems to detect antigen/antibody complexes. Such a system is described in pending U.S. patent application Ser. No. 662,147, which enjoys common ownership and is incorporated herein by reference.

The use of SPM to monitor specific binding reactions can occur in many ways. In one embodiment, one member of a specific binding partner (antibody specific substance which is a suitable LKM antigen such as LKM microsome fraction) is attached to a surface suitable for scanning. The attachment of the antibody specific substance may be by adsorption to a test piece which comprises a solid phase of a plastic or metal surface, following methods known to those of ordinary skill in the art. Or, covalent attachment of a specific binding partner (antibody specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercapto-propyl)-trimethoxy silane (Sigma Chemical Co., St. Louis, Mo.) can be used to introduce reactive groups such as amino-, vinyl, and thiol, respectively. Such activated surfaces can be used to link the binding partner directly (in the cases of amino or thiol) or the activated surface can be further reacted with linkers such as glutaraldehyde, bis (succinimidyl) suberate, SPPD 9 succinimidyl 3-[2-pyridyldithio] propionate), SMCC (succinimidyl-4-[Nmaleimidomethyl] cyclohexane-1-carboxylate), SIAB (succinimidyl [4iodoacetyl] aminobenzoate), and SMPB (succinimidyl 4-[1maleimidophenyl] butyrate) to separate the binding partner from the surface. The vinyl group can be oxidized to provide a means for covalent attachment. It also can be used as an anchor for the polymerization of various polymers such as poly acrylic acid, which can provide multiple attachment points for specific binding partners. The amino surface can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons) (all of which are available from Pharmacia, Piscataway, N.J.), or Ficoll (molecular weight 70,000 daltons (available from Sigma Chemical Co., St. Louis, Mo.). Also, polyelectrolyte interactions may be used to immobilize a specific binding partner on a surface of a test piece by using techniques and chemistries described by pending U.S. patent applications Ser. No. 150,278, filed Jan. 29, 1988, and Ser. No. 375,029, filed Jul. 7, 1989, each of which enjoys common ownership and each of which is incorporated herein by reference. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

A test kit according to the present invention comprises all of the essential reagents required to perform a desired specific fluorescence polarization immunoassay according to the present invention for the quantification of LKM autoantibodies in a test sample. The test kit is presented in a commercially packaged form as a combination of one or more containers holding the necessary reagents, as a composition or admixture where the compatibility of the reagents will allow.

Particularly preferred is a test kit for the fluorescent polarization immunoassay quantification of LKM autoantibody in a test sample, comprising fluorescent tracer compounds and antibodies and a solid phase upon which is coated LKM microsome fragments, as described hereinabove for the quantification of LKM autoantibody. It is to be understood that the test kit can, of course, include other materials as are known in the art and which may be desirable from a user standpoint, such as buffers, diluents, standards, and the like, useful as washing, processing and indicator reagents.

The present invention will now be described by way of examples, which are meant to illustrate, but not to limit, the spirit and scope of the invention.

EXAMPLES

Example 1. Preparation of Microsome Fraction

The microsomal fraction was prepared as described by Meyer zum Büschenfelde and Miescher, *Clin. Exp. Immunol*, Vol. 10: 89–94 (1972).

Example 2. Recombinant LKM and CKS-LKM Proteins

A. Recombinant LKM

The recombinant LKM protein used as capture antigen for the complex formation with patients anti LKM antibodies comprises the amino acids 125–497 of the cytochrome P450 db1 as described by Manns et al., *J. Clin, Invest.* Vol 83: 1066–1072. In addition to this LKM-1 sequence, the first 14 amino acids of the CKS protein (CMP-KDO Synthetase) was fused to the N-terminal side of LKM as described by T. Bolling and W. Mandecki, *Biotechniques*, Volume 8, pages 488–490 (1990) and U.S. Pat. No. 5,124,255, entitled "CKS Method Of Protein Synthesis". For the coating of microparticles an *Escherichia coli* cell lysate was used, which was enriched in the concentration of recombinant protein by performing successive washing steps with 1% Triton® X-100, 1M NaCl and 4M urea.

B. Recombinant CKS-LKM

The fusion protein was created by recloning the cytochrome P450 db1 (LKM-1) sequence (coding for amino acid 125–497, as published by Manns et al., *J. Clin. Invest.* Vol 83: 1066–1072) N-terminally to CKS. The DNA for LKM-1-CKS fusion protein was prepared from the LKM-1 gene by cloning into an expression vector containing the CKS gene under the control of a modified lac promoter as described by T. Bolling and W. Mandecki, *Biotechniques*, Volume 8, pages 488–490 (1990) and U.S. Pat. No. 5,124,255, entitled "CKS Method Of Protein Synthesis". The fusion protein preparation was obtained from lysed *E. coli* by 25 to 35% ammonium sulfate fractionation. Enrichment of recombinant protein is done as described in Example 2A.

Example 3. Preparation of Solid Phase

A. Washing of Solid Phase

A 1 ml of microparticle suspension (Bangs Styrene/Vinyl Carboxylic Acid, 0.216 µm, 10% solids [available from Bangs Laboratories, Carmel, Ind. 46032-2823, U.S.A.) was placed in a test tube. 0.5 g mixed bed resin per one ml of 10% solid microparticles were added and incubated for one and three-quarter hours at room temperature. Following incubation, the microparticle mixture was filtered and washed with five ml of water per one ml of 10% solids. Following this filter and wash step, the microparticles were reconcentrated to 10% solids using MICROCON™ MicroKros syringe filters (available from MICROCON, Laguna Hills, Calif., U.S.A.).

B. Coating Procedure

The following procedure was used to coat the microsome fraction to the microparticles. 200 µl of microparticles washed according to the procedure of Example 3A were added to 750 µl of phosphate buffered saline (PBS: 138 mM NaCl, 2.7 mM KCl, 8.09 mM $Na_2HPO_4$, 1.76 mM $KH_2PO_4$), pH 7.4. Next, 3 µl of Tween-20® was added to the microparticles and mixed for 30 seconds at room temperature. Then, 50 µl of the microsome fraction (protein concentration: 16 mg/ml) or recombinant LKM prepared as described in Example 1 and 2 was sonicated for 5 minutes and added to the reaction mixture to yield a final concentration of 0.8 mg/ml microsomal protein. Immediately following this, 10 µl of 10% 1-Ethyl-3-(3-Dimethylaminopropyl) carbodiimide (EDC) (available from Sigma Chemical Co., St. Louis, Mo., U.S.A.) was added to the reaction mixture and mixed for two hours on an Eppendoff Thermoshaker at 1200 rpm, at room temperature. Next, the reaction mixture (1 ml) containing the microparticles was washed once using 5 ml Tris buffered saline (TBS: 50 mM Tris/HCl, pH 7.5, 150 mM NaCl) containing 0.1% sodium azide using MICROGON MicroKros syringe filters. After the second wash step the microparticles were resuspended in TBS containing 1% bovine serum albumin (BSA, Labor Neidig, Schönbrunn/Germany) and 0.1% sodium azide to a final concentration of 0.1% solids (coated microparticles).

Example 4. Assay Procedure

The following assay was performed in the IMx® system analyzer, using disposable reagents and test devices, all are available from Abbott Laboratories, Abbott Park, Ill. The test serum was manually diluted to 1:1000 in diluent buffer (available in Abbott HCV 2nd Generation Assay, code number 4A14F, from Abbott Laboratories, Abbott Park, Ill.). Next, 150 µl of the diluted test serum was manually placed in the IMx® predilution well. 50 µl of microparticles prepared as described in Example 3A and 3B and 60 µl of the diluted serum was automatically transferred to the reaction well, and 30 µl of MEIA -buffer (available from Abbott Laboratories, Abbott Park, Ill., U.S.A.) was automatically added. The reaction mixture was incubated for 20 minutes at 35° C. Then, 90 µl of the reaction mixture (containing microparticles/diluted serum and MEIA buffer) was automatically transferred to the filter. The filter was washed automatically with 200 µl of MEIA buffer. Then, 65 µl of conjugate (goat- anti-human IgG-alkaline phosphatase conjugate, diluted in conjugate diluent buffer (available from Abbott Laboratories, Abbott Park, Ill., U.S.A.) was automatically added to the filter. This reaction mixture was incubated for 5 minutes at 35° C. Following this incubation, the filter was automatically washed three times with 50 µl of MEIA buffer, and a final time with 100 µl of MEIA buffer. Next, 50 µl of MUP-solution was added to the filter, and the enzyme activity detectable as fluorescence was measured by the $IM_x$® instrument.

Example 5. Comparison of Reactivity of Autoimmune Sera in an Automated System with Microparticles Coated with Different Liver Cell Antigens Porcine liver was homogenate was separated by differtial ultracentrifugation. The first pellet P1 contained mainly nuclei and crude cell membrane fragments. The supernatant was recentrifuged at higher speed leading to the P2 pellet, which contained mainly heavy mitochondria. The same step was repeated with the second supernatant at higher speed yielding pellet 3 (P3), which contained mainly light mitochondria. The centrifugation of the third supernatant at higher speed yielded P4, containing the microsomes, little vesicles spontaneously formed from fragments of the endoplasmic reticulum.

Figure 2:
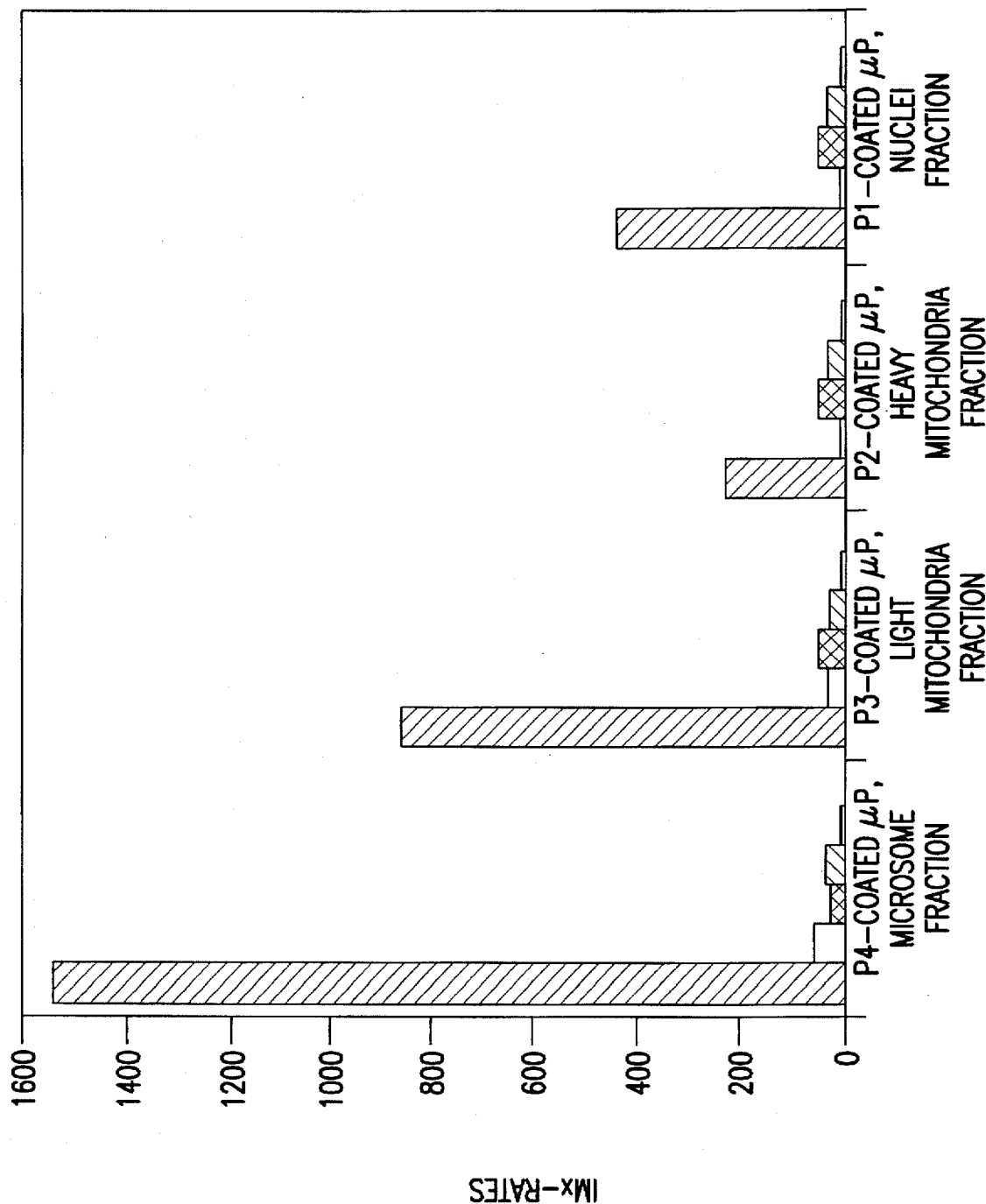
FIG. 2 is a graph of the reactivity of autoimmune sera in an automated assay with microparticles coated with different liver cell antigens.

The 4 pellets, resuspended in PBS buffer, were used for coating microparticles as described in Example 3B. The coated microparticles were tested on the $IM_x$® analyzer as described previously hereinabove in Example 4. Referring to FIG. 2, the bars show the average $IM_x$® rate using 5 sera of ■ strong anti-LKM positive, □ weak anti-LKM positive, ▣ anti-mitochondrial antibody (AMA) positive, ▨ anti-nuclear antibody (ANA) positive and ■ autoantibody negative control sera tested on microparticles coated with either microsomal fraction (P4), light (P3) or heavy (P2) mitochondrial or nuclear (P1) fraction of porcine liver cells. P4 material coated to the microparticles show the best specificity for the anti-LKM antibodies. on these microparticles even the weak anti-LKM sera showed still higher rates than the AMA and ANA sera. The highest reactivity to AMA can be seen in P2 and P3, the mitochondrial fractions, but also in the P1 fraction, what may be due to not-lysated cells containing mitochondria. Reactivity of ANA sera is highest at P2 and P1, in the nuclei containing fraction.

Example 6. Correlation of RIA-titers to Rates Obtained in an Automated System

Figure 3:
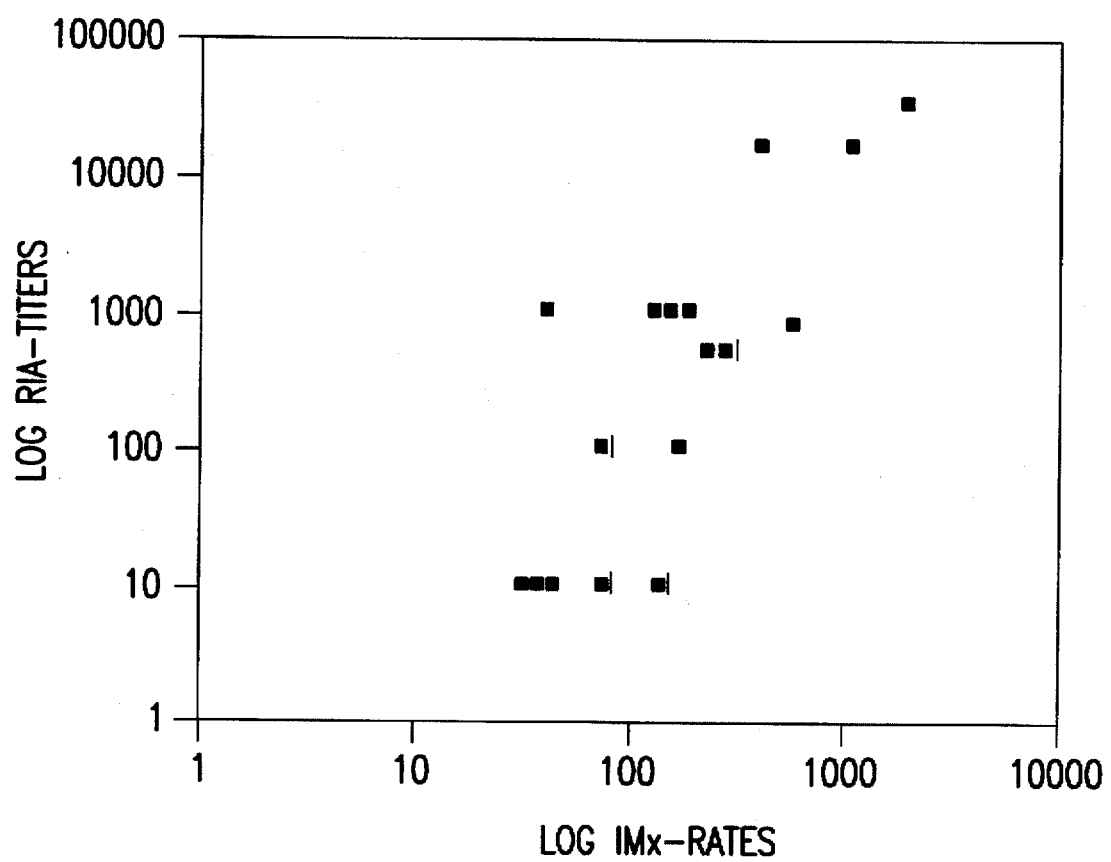
FIG. 3 is a graph which correlates RIA titers to rates obtained using the Abbott IMx® system, in which the log of the RIA titers is plotted on the Y axis and the log of the IMx® rates is plotted on the X axis.

Eighteen anti-LKM positive sera previously tested with an anti-LKM radioimmunoassay (RIA) were tested in the anti-LKM $IM_x$® assay. The microparticles were coated as described in Example 3, using porcine microsomes. The test was done as described hereinabove in Example 4 using the $IM_x$® analyzer. Referring to FIG. 3, the logs of the RIA titers (1:log Y value) of the 18 sera on the Y axis were plotted against the logs of the $IM_x$® rates (log counts per counts per second) on the X axis to show the correlation between the results yielded by the two different assays. The results yielded by the $IM_x$®-assay correlated very well with the results of the RIA. The coefficient of correlation is r=0.94.

Figure 4:
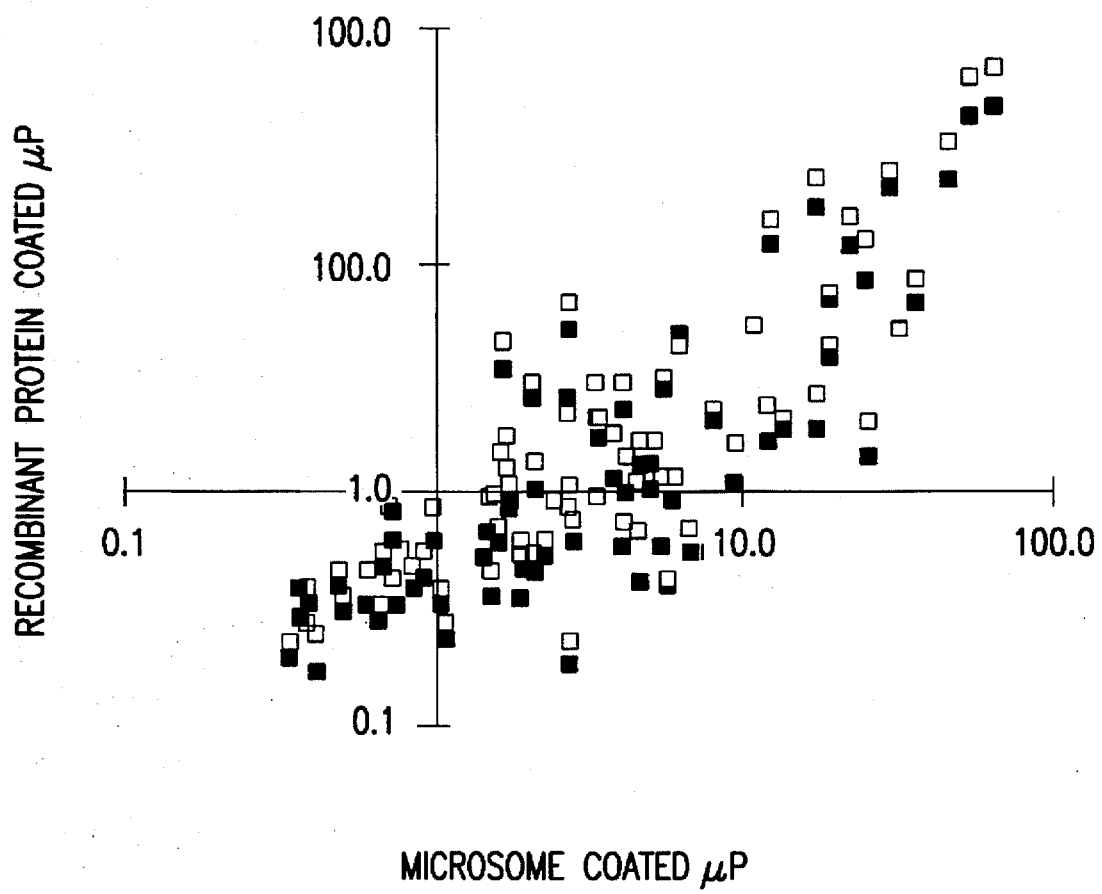
FIG. 4 is a graph which correlates anti LKM measurement results obtained by microsome coated to recombinant LKM-1 coated microparticles, in which the recombinant protein coating is plotted on the Y axis and the microsome fraction coating is plotted on the X axis.

Next, 78 sera known to be positive for anti-LKM by Immunofluorescence assay on tissue slides were tested in the $IM_x$® analyzer using 1.: microparticles coated with microsomes, 2.: with recombinant LKM, and 3.: with recombinant CKS-LKM. The coating was done as described hreinabove in Examples 1–3; all antigen were coated with an antigen concentration of 0.5 mg/ml. The test in the $IM_x$®-analyzer was done as described hereinabove. The results received using the recombinant proteins correlated very well with the results received using the microsomes. Referring to FIG. 4, in the graph, the log of IMx rates yielded after analyzing 78 patients for anti LKM antibodies using either microsomes coated microparticles plotted on the X axis against the log of the rates received using the two different recombinant proteins (■ rec.LKM, □ rec.CKS-LKM) on the Y axis.

The correlation coefficient for:
microsomes/rec.CKS-LKM was r=0.866
microsomes/rec.LKM was r=0.872.
The coefficient of correlation comparing both recombinant proteins was r=0.996 (not shown on the graph).

Figure 5A:
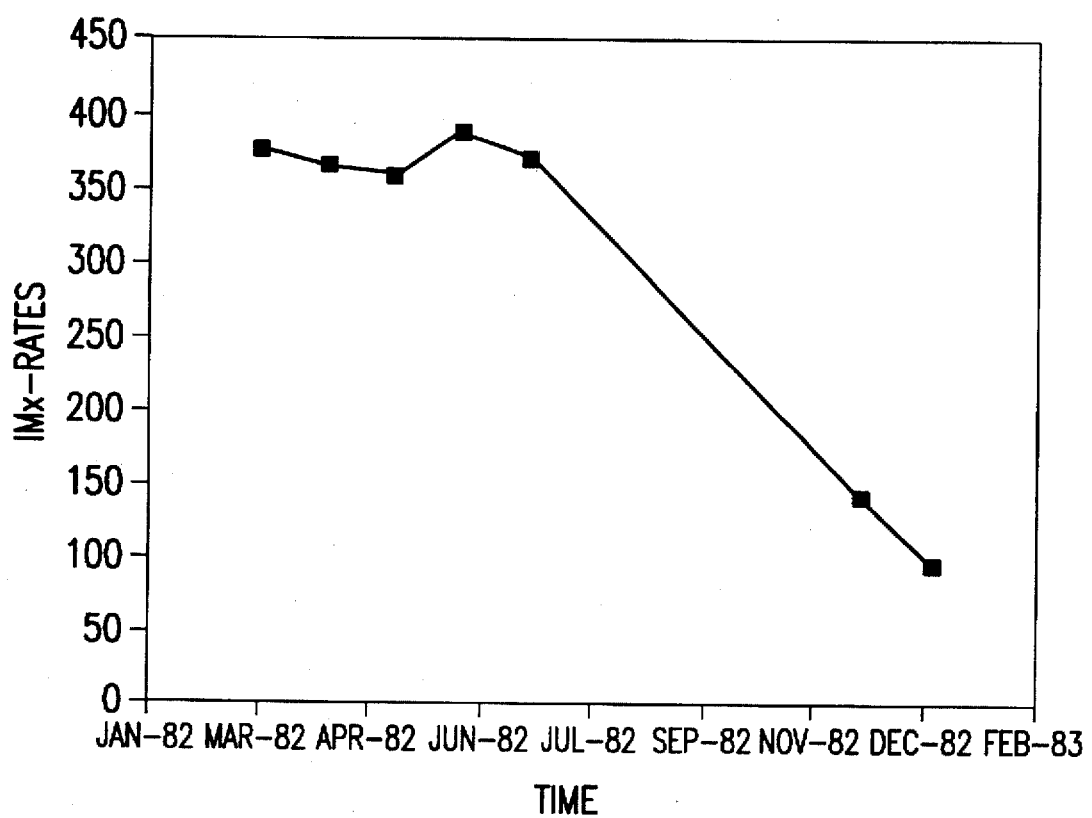
FIG. 5 are two graphs (A and B) which show the monitoring of a immunosuppresse therapy.
Figure 5B:
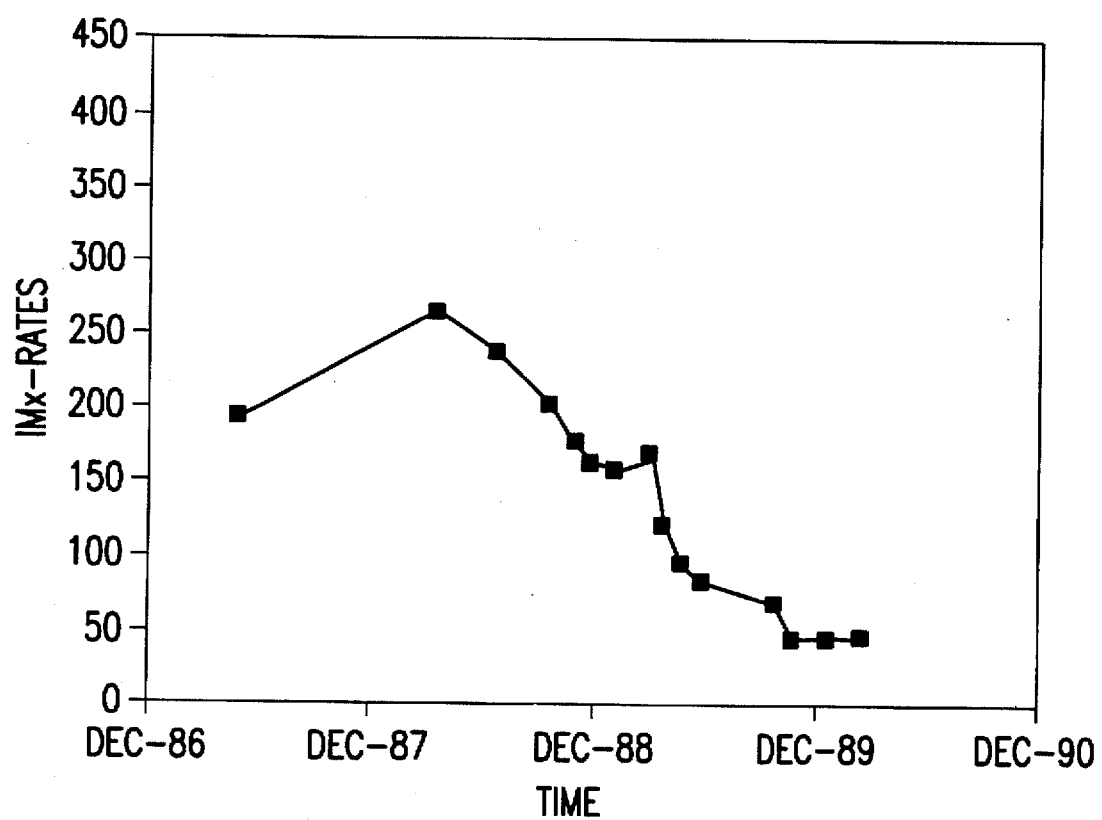

Example 7. Monitoring of anti LKM antibodies positive patients during immunosuppressive therapy with the anti LKM IMx assay Blood samples from two patients with Autoimmune Hepatitis, who were treated with immunosuppressive therapy, were drawn at fixed time points and stored at −20° C. for farther characterization. The analyzation of the anti-LKM titers were performed as described hereinabove in Examples 1–4. Referring to FIGS. 5A and 5B LKM titers (IMx rates) (Y axis) versus time (X axis) over a period of time of a A: 9 months and B: 3 years during treatment of Autoimmune Hepatitis patients are shown. In correlation with improvement of clinical condition of the patients, a decline of anti LKM titers was observed when using the anti LKM assay method of the invention.

Those skilled in the art can contemplate reaction conditions, timing schemes and signal deconvolution algorithms to determine more than two analytes in the same assay procedure upon consideration of the teachings provided by the present invention. These choices thus are considered within the scope of the present invention.

We claim:

1. A method for determining anti-LKM (anti-liver-kidney microsomal) autoantibody which may be present in a test sample, said method comprising:
   (a) incubating the test sample with an LKM specific binding member attached to a solid phase for a time and under conditions sufficient for LKM antigen/anti-LKM antibody specific binding pairs to form;
   (b) incubating the so-formed specific binding pairs with an indicator reagent comprising a species-specific antibody attached to a signal generating compound capable of generating a measurable signal;
   (c) measuring the signal detected,
wherein the amount of signal detected is correlated to the amount of anti-LKM antibody present in the test sample, and wherein said LKM specific binding member is an LKM-1 antigen selected from the group consisting of LKM microsome fraction and recombinant LKM-1 (cytochrome P450 db 1) amino acids 125–497.

2. The method of claim 1 wherein the solid phase comprises a suspension of microparticles.

3. The method of claim 1 wherein the test sample is diluted prior to performing step (a).

4. The method of claim 2 further comprising the step of separating the solid phase comprising LKM antigen/anti-LKM antibody before performing step (b) by microparticle separation of specific binding pairs on a porous element and washing said solid phase.

5. The method of claim 1 wherein said signal generating compound of step (b) is alkaline phosphatase.

6. The method of claim 1 wherein said species-specific antibody is goat anti-human IgG.

7. A test kit for performing an LKM autoantibody assay, said test kit comprising:
   (a) a container containing LKM antigen selected from the group consisting of an LKM microsome fraction and LKM-1 cytochrome p450 db 1 amino acids 125–497 bound to a solid phase; and
   (b) a container containing an indicator reagent capable of generating a measurable signal.

8. The test kit of claim 7 wherein said solid phase of (a) are microparticles.

9. The test kit of claim 7 wherein said indicator reagent is goat anti-human IgG attached to alkaline phosphatase.

* * * * *